United States Patent [19]  [11] 4,296,131
Ladage et al.  [45] Oct. 20, 1981

[54] PHARMACEUTICAL COMPOSITIONS AND THEIR USE IN THE PROPHYLAXIS AND/OR TREATMENT OF CERTAIN DISEASES

[75] Inventors: Cornelis A. Ladage, De Meern; Douwe J. Van Linge, Eemnes; Huibert A. Van Riessen, Lunteren, all of Netherlands

[73] Assignee: ACF Chemiefarma N.V., Maarssen, Netherlands

[21] Appl. No.: 65,627

[22] Filed: Aug. 10, 1979

Related U.S. Application Data

[62] Division of Ser. No. 3,968, Jan. 16, 1979, Pat. No. 4,250,089.

[30] Foreign Application Priority Data

Jan. 20, 1978 [NL] Netherlands ................ 7800762

[51] Int. Cl.$^2$ .................. A61K 31/055; A61K 47/00
[52] U.S. Cl. .................................... 424/347; 424/365
[58] Field of Search ........................... 424/347, 365

[56] References Cited

U.S. PATENT DOCUMENTS 2,812,283 11/1957 Geschickter et al. ............. 167/82
3,551,554 12/1970 Herschler ........................... 424/7

FOREIGN PATENT DOCUMENTS 1073365 6/1967 United Kingdom .

Primary Examiner—Donald B. Moyer
Attorney, Agent, or Firm—Curtis, Morris & Safford

[57] ABSTRACT

The invention relates to a solvent vehicle for therapeutics comprising a dialkyl ester of adipic acid and, optionally, DMSO, which is particularly useful for therapeutic materials having a low solubility or being insoluble in water.

The invention further relates to pharmaceutical compositions which are suitable for parenteral administration, especially by intramuscular injection, comprising a therapeutically active material dissolved in said solvent vehicle.

Solvent vehicles containing di-n-butyl adipate and DMSO and, if desired, one or more adjuvants, are preferred.

Particularly useful are pharmaceutical compositions for the prophylaxis and/or treatment of diseases caused by internal parasites, which can be administered by intramuscular injection. A preferred embodiment of the invention is an injectable composition against distomatosis (liver fluke disease) containing proportionally 12.5 g 4,6'-dichloro-4',6-dinitro-2,2'-methylenediphenol and 30 g of DMSO, completed with di-n-butyl adipate to 100 cm$^3$.

8 Claims, No Drawings

PHARMACEUTICAL COMPOSITIONS AND THEIR USE IN THE PROPHYLAXIS AND/OR TREATMENT OF CERTAIN DISEASES

This is a divisional application of Ser. No. 3,968, filed Jan. 16, 1979, now U.S. Pat. No. 4,205,089, granted May 27, 1980.

The present invention relates to novel liquid pharmaceutical compositions comprising a drug and a vehicle, which are suitable for parenteral administration to warm-blooded beings, especially by intramuscular injection.

More particularly, the invention relates to certain compounds or combinations of compounds which have been found to be excellent solvents and vehicles for therapeutic materials having a low solubility or being insoluble in water.

The pharmaceutical formulations and compositions of the invention have been found to be effective in combating certain diseases, of which particularly distomatosis or liver fluke disease may be mentioned.

Distomatosis is a parasitic affection of the liver, which is incident to mammals and especially to cattle and sheep, and which sometimes victimizes even men. The disease is caused by the liver fluke, notably by the Fasciola hepatica and Fasciola gigantica. The infestation of cattle and sheep with liver flukes causes considerable damage to national economy as can be seen from statistics. For example, the economic losses in Germany, the United Kingdom, the Netherlands and the U.S.A. (Oregon) have been estimated at DM 300,000,000,—, 50,000,000,—, Dfl 200,000,000,— and $ 4½–11,000,000,— a year, respectively. (W. Heeschen et al, Arch. Lebensmitt. Hyg. (1972) 23, 1–7; Vet. Rec. (1974) 95, 75; G. Froyd and N. McWilliam, Proc. 20th World Vet. Congress 1975, vol. 1, 553–556; Report of the Nationale Raad voor Landbouwkundig Onderzoek, "Ontwikkelingsplan dierlijke produkten" (1976), Part II, 199; T. P. Kistner, J. Amer. Vet. Med. Ass. (1977) 171, 224–226).

Many remedies against distomatosis have been known already. Among them are commercial products, comprising as active ingredient bromophenophos, hexachlorophene, niclosulide, menichlopholan, bithionol, disophenol or nitroxynil and certain compounds not commercialised so far, for example those which have been described in Dutch Pat. No. 152.452 or in Dutch Patent Application No. 71.04839. Many physiologically active anti-liver fluke agents hitherto known are phenol derivatives, which are poorly soluble or insoluble in water. By phenol derivatives we mean compounds comprising one or more substituted or unsubstituted phenol groups or derivatives thereof.

Most remedies against liver fluke are therefore formulated as tablets or suspensions for oral administration. However, this oral administration is very cumbrous, particularly in treating large numbers of animals. Besides, the oral administration of medicines to bigger animals is often accompanied by considerable difficulties.

Therefore, many efforts have been made to develop a pharmaceutical formulation against liver fluke for parenteral administration and preferably by injection. With regard to all injectable formulations hitherto known it has appeared, however, that a number of adverse effects occur, so that these formulations are less suitable or even unsuitable as injectable solutions against liver fluke.

Among the most important adverse effects are local reactions, which become apparent inter alia as inflammations and necrosis of the local tissue, and reduced bio-availability.

The reduced bio-availability, for instance, may be caused by the development of intramuscular depots, that is to say that the active substance is not or insufficiently resorbed from the injection site. These intramuscular depots are most undesirable because they may cause irregular plasma concentration levels, which do not improve the recovery of the animals or make them unfit for slaughtering for a long time. Moreover, there is a risk that such intramuscular depots will be consumed along with the meat. The formation of a depot often involves crystallization of the active compound.

Attempts have been made to eliminate these harmful effects by adding emulsifying agents with stabilizing properties, such as polyoxyethylated castor-oil, to the injectable formulations. These attempts, however, remained unsuccessful, because the active compounds used appeared to be too toxic for the tissue.

Furthermore, it appeared that solutions of salts of active compounds are nearly always too hypertonic, as a result of the high concentrations which are often necessary. Consequently, these solutions are also unsuitable for parenteral administration.

It is also known that a number of active compounds are unsuitable for parenteral administration, because they are unstable in the vehicles which are commonly used.

It has been proposed in U.S. Pat. No. 2,812,283 to use combinations of certain alkyl esters of cis-$\Delta^4$-tetrahydrophthalic acid and vegetable oils as solvents and vehicles for therapeutic materials, both for injection purposes and oral administration.

It is known from U.S. Pat. No. 3,551,554 to enhance the tissue penetration of physiologically active agents by conjointly applying them to the tissue with dimethyl sulfoxide (DMSO). According to said patent antineoplastic agents, steroids, central system-active agents, local anaesthetics, anti-inflammatory agents, diagnostic dyes and radiopaque agents, and vasodilators may be advantageously administered by injection with DMSO in concentrations preferably up to 20% by weight to enhance penetration of internal tissue membrane barriers to achieve better distribution of these agents.

All parenteral formulations which have been described in said patent contained besides DMSO at least water as the solvent.

No reference has been made to the use of DMSO in anti-parasitic formulations. It will also be clear to those skilled in the art that the para-aminophenol derivatives acetanilid, acetophenetidin and acetaminophen, which have been mentioned as analgesics, have a structure different from the phenol derivatives mentioned hereinbefore in relation to the anti-liver fluke agents.

Finally, it is known from Dutch Patent Application No. 66.02118 that certain hexapeptides show a prolonged periferic vasodilating activity, when dissolved in a suitable solvent, such as diacetine, DMSO and dimethyl acetamide, to form injectable solutions.

It is an object of the invention as claimed to provide a vehicle for therapeutic materials, particularly for those materials which are poorly soluble or insoluble in water. It is a further object of the invention to provide a pharmaceutical composition comprising a therapeutic agent and said vehicle, which can be administered parenterally and preferably by intramuscular injection.

We have now found that certain dialkyl esters of adipic acid are excellent solvent vehicles for therapeutic materials and that these compounds and pharmaceutical compositions containing them may be used in the prophylaxis and/or treatment of certain diseases.

Accordingly, the invention provides a solvent vehicle comprising a symmetrical or unsymmetrical dialkyl ester of adipic acid, wherein the number of carbon atoms in the two alkyl groups together may vary between six and twelve. In the case of the unsymmetrical esters, however, the smaller alkyl group should contain at least two carbon atoms, since the methyl esters have not proven particularly effective.

Suitable dialkyl esters of adipic acid are, for example, di-n-propyl adipate, di-isopropyl adipate, di-n-butyl adipate, di-isobutyl adipate, di-sec-butyl adipate, di-n-pentyl adipate or ethyl-n-hexyl adipate. Of these di-n-butyl adipate is most preferred.

It will be realized, that most of the dialkyl esters of adipic acid as defined hereinbefore are known compounds per se. The use of said compounds in solvents and vehicles for therapeutic agents, however, is believed to be novel and surprising.

The above compounds have been found to be particularly useful solvents for therapeutic agents, if they are combined with DMSO and, if desired, with one or more adjuvants. The addition of DMSO to the vehicle generally improves the solubility of the therapeutic agents further.

The present invention also provides a pharmaceutical composition comprising a therapeutic agent in an effective amount and a solvent vehicle as defined hereinbefore. Said compositions have been found to be effective in parenteral administration, particularly if injected intramuscularly, in that they have a better tolerance and show an excellent bioavailability, with the active compound being resorbed from the injection site in a short time. The compositions comprising di-n-butyl adipate as a vehicle are preferred.

We have also found, that the properties of the pharmaceutical compositions of the invention may be improved further, if the formulations contain besides a dialkyl adipate also DSMO and, if desired, one or more adjuvants.

In this way the solubility of the active compound in the solvent vehicle is promoted, while generally these formulations show a still better tolerance and bio-availability after administration as compared with the formulations without DMSO. The compositions comprising DMSO are therefore preferred.

Among the adjuvants which may be used in the pharmacological compositions are, for example, surfactants or wetting agents, such as a polysorbatum (e.g. the commercial product Tween 80); acids, such as oleic acid, lactic acid or adipic acid; other lipophilic ingredients, e.g. mixtures of triglycerides, such as the commercial products Novata, Estarine, Miglyol and Myritol 318; oils, such as castor-oil; other esters; alcohols, such as cetyl alcohol, polyvinyl alcohol or the commercial product Eutanol G.

The favourable properties of the pharmaceutical compositions offered by the invention manifest themselves particularly in the use as injectable therapeutics for the prevention and control of distomatosis.

As already put forward, the active ingredient in such compositions is mostly a phenol derivative, which is often poorly soluble or insoluble in water. Most suitable are the compositions comprising as a therapeutic agent against distomatosis a o,o'-bisphenol derivative or, preferably, a 2,2'-methylenediphenol derivative.

Examples of suitable o,o'-bisphenol derivatives are 4,4'-dichloro-6,6'-dinitro-o,o'-bisphenol (menichlopholan) and 4,4',6,6'-tetrabromo-o,o'-bisphenol.

Examples of suitable 2,2'-methylenediphenol derivatives are 4,6'-dihalogen-4',6-dinitro-2,2'-methylenediphenols, in particular 4,6'-dichloro-4',6-dinitro-2,2'-methylenediphenol (hereinafter referred to as "active compound A") and 6-bromo-4'-fluoro-4,6'-dinitro-2,2'-methylenediphenol.

The pharmaceutical compositions of the invention which are effective against distomatosis usually contain 1–50% w/v, preferably 5–25% w/v and more preferably 10–15% w/v of a pharmacologically active agent. The exact amount depends mainly on the nature of the therapeutic agent to be used, in which respect factors like activity of the agent, solubility of said agent in the solvent vehicle, size of the organism to be treated and volume of the pharmaceutical formulation to be administered may play a part.

Preferably, the pharmaceutical compositions of the invention also contain 5–50% w/v, in particular 20–40% w/v and more in particular about 30% w/v of DSMO. the exact amount may depend on factors such as the therapeutically active compound to be used, the solvent vehicle and the desired availability.

A preferred embodiment of the invention is a pharmaceutical composition comprising the active compound A in a solvent vehicle of di-n-butyl adipate and DMSO and, if desired, one or more adjuvants.

The compositions containing 5–30% w/v of the active compound A and 5–50% w/v, particularly 20–40% w/v of DMSO, in di-n-butyl adipate are preferred.

An especially preferred composition is that containing proportionally 12.5 g of active compound A and 30 g of DMSO, completed with di-n-butyl adipate to 100 cm$^3$.

Said pharmaceutical compositions are particularly suitable for administration to mammals by intramuscular injection. Contrary to what was hitherto usual in veterinary medicine with respect to the treatment of distomatosis, it is sufficient to administer a single dose of a composition of the invention by intramuscular injection in order to achieve a complete cure, because local reactions and intramuscular depots completely or nearly completely fail to develop.

The compositions of the invention may be prepared according to methods which are fully known to those skilled in the art. For example, the compositions may be prepared by adding the ingredients of a desired formulation in an arbitrary sequence, thus forming a mixture which will result in a clear solution by continuous stirring. Preferably, the therapeutic agent is first wetted by a part of the dialkyl adipate, to be used as the vehicle, then DMSO is added, if this forms part of the composition, whereafter possible adjuvants are dissolved. The addition of another part of the dialkyl adipate completes the procedure. The mixture is intensively stirred after the addition of each ingredient or while adding the ingredients. The stirring is continued till all ingredients are dissolved. The mixture is preferably stirred in a closed vessel provided with a fast rotating device.

If desired, the solution may be sterilized in a manner as commonly used, for example by heating or by filtering through a millipore filter. The various pharmaceutical forms are desirably provided in determined amounts, as in containers of a given volume. Thus, for example, graduated vials containing, say 500 cm³ of a composition according to the invention may be provided.

As is common practice, the compositions will usually be accompanied by written or printed directions for use in the medical treatment concerned.

The invention also relates to the use of a pharmaceutical composition, as described hereinbefore, in the prophylaxis and/or treatment of certain diseases, particularly diseases caused by internal parasites, for example distomatosis or liver fluke disease.

A further aspect of the invention is to provide a method of prophylaxis and/or treatment of certain diseases in mammals, which comprises the parenteral administration to the sufferer of a pharmaceutical composition according to the invention, as described hereinbefore.

The following examples further illustrate the invention.

EXAMPLE I 4,6'-Dichloro-4',6-dinitro-2,2'-methylenediphenol (compound A), 25 kg, was wetted in a pressure vessel of stainless steel by addition of 6 kg of di-n-butyl adipate. This mixture was stirred mechanically for 2 minutes. Then 60 kg of DMSO was added, whereafter the mixture was intensively stirred mechanically till compound A was dissolved. After this di-n-butyl adipate was added to a volume of 200 l.

The solution was homogenized by mechanically stirring for 5 minutes and was then led under pressure with oxygen-free nitrogen over a millipore filter (Selectron TE35, 0.2 μm).

The composition was prepared in the absence of direct sunlight and at a relative humidity of less than 37%. The obtained solution was poured in appropriate vials.

In a similar manner the following compositions were prepared:

EXAMPLE II

| Compound A | 12.5% w/v |
|---|---|
| DMSO | 12.5% w/v |
| di-n-butyl adipate | ad 100 cm³ |

EXAMPLE III

| Compound A | 12.5% w/v |
|---|---|
| DMSO | 20% w/v |
| di-n-butyl adipate | ad 100 cm³ |

EXAMPLE IV

| Compound A | 20% w/v |
|---|---|
| DMSO | 20% w/v |
| di-n-butyl adipate | ad 100 cm³ |

EXAMPLE V

| Compound A | 20% w/v |
|---|---|
| DMSO | 30% w/v |
| di-n-butyl adipate | ad 100 cm³ |

EXAMPLE VI

| Compound A | 20% w/v |
|---|---|
| DMSO | 40% w/v |
| di-n-butyl adipate | ad 100 cm³ |

EXAMPLE VII

| Compound A | 12.5% w/v |
|---|---|
| DMSO | 12.5% w/v |
| Novata AB | 6.25% w/v |
| di-n-butyl adipate | ad 100 cm³ |

The Novata was dissolved under heating in a small amount of di-n-butyl adipate and this solution was added to the solution of compound A in DMSO. Then di-n-butyl adipate was added to a volume of 100 cm³. Similarly, the following compositions were prepared:

EXAMPLE VIII

| Compound A | 12.5% w/v |
|---|---|
| DMSO | 12.5% w/v |
| Novata AB | 6.25% w/v |
| lactic acid | 0.75% w/v |
| di-n-butyl adipate | ad 100 cm³ |

EXAMPLE IX

| Compound A | 12.5% w/v |
|---|---|
| DMSO | 12.5% w/v |
| Novata AB | 6.25% w/v |
| oleic acid | 0.75% w/v |
| di-n-butyl adipate | ad 100 cm³ |

EXAMPLE X

| Compound A | 12.5% w/v |
|---|---|
| DMSO | 12.5% w/v |
| Novata AB | 6.25% w/v |
| Tween 80 | 0.75% w/v |
| di-n-butyl adipate | ad 100 cm³ |

EXAMPLE XI

| Compound A | 12.5% w/v |
|---|---|
| DMSO | 12.5% w/v |
| cetyl alcohol | 1% w/v |
| di-n-butyl adipate | ad 100 cm³ |

EXAMPLE XII

| Compound A | 12.5% w/v |
|---|---|
| DMSO | 12.5% w/v |
| castor-oil | 25% w/v |
| di-n-butyl adipate | ad 100 cm³ |

EXAMPLE XIII

| Compound A | 1% w/v |
|---|---|
| ethyl-n-hexyl adipate | ad 100 cm³ |

EXAMPLE XIV

| Compound A | 12.5% w/v |
|---|---|
| DMSO | 12.5% w/v |
| di-n-pentyl adipate | ad 100 cm³ |

EXAMPLE XV

| 4,4',6,6'-tetrabromo-o,o'-bisphenol | 20% w/v |
|---|---|
| DMSO | 30% w/v |
| di-n-butyl adipate | ad 100 cm³ |

EXAMPLE XVI

| 4,4',6,6'-tetrabromo-o,o'-bisphenol | 15% w/v |
|---|---|
| di-n-butyl adipate | ad 100 cm³ |

EXAMPLE XVII

| Dimethyl ester of compound A | 17.5% w/v |
|---|---|
| DMSO | 17.5% w/v |
| di-n-butyl adipate | ad 100 cm³ |

EXAMPLE XVIII

| Dimethyl ester of compound A | 4% w/v |
|---|---|
| di-n-butyl adipate | ad 100 cm³ |

EXAMPLE XIX

| Lidocaine | 4% w/v |
|---|---|
| DMSO | 25% w/v |
| di-n-butyl adipate | ad 100 cm³ |

EXAMPLE XX

| Cortisone | 5% w/v |
|---|---|
| DMSO | 50% w/v |
| di-n-butyl adipate | ad 100 cm³ |

The following experiments illustrate the tolerance and bio-availability found during the use of some pharmaceutical compositions described in the examples. The experiments were carried out in cattle, to which the compositions concerned had been administered by intramuscular injection. The number of the compositions set forth hereinafter, corresponds with the number of the example in which the preparation of the said composition is described.

EXPERIMENT A

1. Local reactions

To 98 cows of different races, with a weight varying from 200 to 700 kg, composition I was administered by intramuscular injection in the neck muscles. The dosage of compound A was 3 mg/kg body weight.

Besides, 6 animals were injected with 12 ml of di-n-butyl adipate, containing only 30% g/v DMSO.

The animals were monitored for local reactions during 33–36 days, initially every 24 hours and after about 5 days at greater intervals.

The local reactions were marked as follows:

| − | :absent |
|---|---|
| ± | :some hardening of the muscle tissue (palpable) |
| + | :visible (acceptable) |
| ++ | :moderate (only acceptable if lasting not longer than 1–2 days) |
| +++ | :serious |
| ++++ | :severe |
| 0 | :hard tubercle |

No local reaction developed in 77 cows (−). In 21 animals local reactions were found, of which 10 were negligible (±) and 8 visible (+). The remaining 3 animals showed moderate reactions (++), which were reduced to (+) within 24 hours. Nine reactions appeared during 1 day, one reaction (+) persisted for 11 days. The other reactions disappeared after 2–4 days. Five animals showed a temporary painfulness of the neck between 24 and 48 hours after the injection; in 3 of these animals no local reactions was determined.

The different races in which the experiments were carried out, were: Groninger Blaarkop, Dutch-Friesian, Maas-Rijn-IJsel and Jersey. It was remarkable that no local reactions were observed in the 25 experiments with Jerseys, because this race is sometimes hypersensitive to injection.

The 6 animals which were injected with the DMSO/di-n-butyl adipate solution, did not show any local reaction.

2. Bio-availability

In order to determine the bio-availability of active compound A in composition I, this composition was injected intramuscularly in 6 cows; subsequently the concentration of compound A was determined at several time intervals. The determination took place spectrofotometrically, after extraction of the active compound from the plasma.

The bio-availability of compound A is determined by the following pharmacokinetic parameters:

| n | :number of animals |
|---|---|
| r | :correlation coefficient |
| $t_{\frac{1}{2}}$ | :elimination half life of compound A from the plasma (hours) |
| $t_{max}$ | :time at which the maximum plasma concentration of compound A is reached (hours) |
| $C_{max}$ | :maximum plasma concentration of compound A (mg/l) |

The correlation coefficient is a measure for the correlation between the measuring points found and the curve, starting from the one-compartment model.

| Composition | dose mg/kg | n | r | $t_{\frac{1}{2}}$ (h) | $t_{max}$ (h) | $C_{max}$ (mg/kg) |
|---|---|---|---|---|---|---|
| I | 3 | 6 | −0.99 | 59.5 | 25 | 17 |

EXPERIMENT B

1. Local reactions

Composition II was administrated intramuscularly in the neck muscles of 20 cows with a body weight of about 500 kg. The volume of injection was 12 ml.

No reaction was found in 14 cows (−), one cow showed some hardening of the muscle tissue (±), 4 cows showed a visible reaction (+), while a short moderate reaction (++) was observed in one cow.

2. Bio-availability

For the determination of the bio-availability the plasma concentration levels of 6 cows were corrected to a dose of 3 mg/kg.

Result:

| Composition | dose mg/kg | n | r | $t_{\frac{1}{2}}$ (h) | $t_{max}$ (h) | $C_{max}$ (mg/kg) |
|---|---|---|---|---|---|---|
| II | 3 | 6 | −0.99 | 60.5 | 24 | 14 |

EXPERIMENT C

1. Local reactions

Composition III was injected into the neck muscles of 20 cows with different body weights. The volume of injection was 12 ml.

No reaction was found in 4 cows (−), 8 animals showed a short hardening of the muscle tissue after 48 hours (±), 5 cows showed a short visible reaction (+), while in 3 cows a moderate reaction (++) was observed, which appeared rather later (after about 10 days) and disappeared after a few days.

Though sometimes given in a strong overdose (about 7.5 mg/kg), this formulation was well tolerated.

2. Bio-availability

For the determination of the bio-availability the plasma concentration levels of 6 cows were corrected to a dose of 3 mg/kg.

Result:

| Composition | dose mg/kg | n | r | $t_{\frac{1}{2}}$ (h) | $t_{max}$ (h) | $C_{max}$ (mg/kg) |
|---|---|---|---|---|---|---|
| III | 3 | 6 | −0.99 | 67.8 | 30 | 15 |

EXPERIMENT D

1. Local reactions

In 25 cows with a body weight of about 450–500 kg 12 ml of composition IV were injected into the neck muscles of each cow. This corresponds with a dose of about 5 mg/kg.

In 14 cases no reaction was found (−), in 3 cases some hardening of the muscle tissue was determined (±). A visible reaction was observed in 4 cows (+), while in 4 other cows a short moderate reaction was found (++).

2. Bio-availability

Result:

| Composition | dose mg/kg | n | r | $t_{\frac{1}{2}}$ (h) | $t_{max}$ (h) | $C_{max}$ (mg/kg) |
|---|---|---|---|---|---|---|
| IV | 5 | 5 | −0.99 | 66.1 | 40 | 20 |

EXPERIMENT E

1. Local reactions

In 21 cows with a body weight of about 450 kg 12 ml of composition V were injected into the neck muscles of each cow. This corresponds with a dose of about 5 mg/kg.

In 17 cases no reaction was observed (−), in 1 case some hardening of the muscle tissue developed (±) and in 3 cases a short visible reaction was observed (+).

In 20 cows with a body weight of about 500 kg 7 ml of composition V were injected into the neck muscle of each cow. This corresponds with a dose of about 3 mg/kg.

In 15 cases no reaction developed (−), in one case some hardening of the muscle tissue was observed, while 4 cows showed a short visible reaction (+).

2. Bio-availability

Result:

| Composition | dose mg/kg | n | r | $t_{\frac{1}{2}}$ (h) | $t_{max}$ (h) | $C_{max}$ (mg/kg) |
|---|---|---|---|---|---|---|
| V | 5 | 6 | −0.99 | 74.4 | 56 | 19 |
| V | 3 | 6 | −0.99 | 69.2 | 35 | 14 |

EXPERIMENT F

1. Local reactions

In 20 cows with a body weight of 250–500 kg 7 ml of composition VI were injected, corresponding with a dose of about 5.6–2.8 mg/kg.

In 7 cows no reaction was observed (−), 11 cows showed visible reactions (+), while in two cases short moderate reactions were observed (++).

2. Bio-availability (corrected to a dose of 3 mg/kg)

Result:

| Composition | dose mg/kg | n | r | $t_{\frac{1}{2}}$ (h) | $t_{max}$ (h) | $C_{max}$ (mg/kg) |
|---|---|---|---|---|---|---|
| VI | 3 | 6 | −0.99 | 66.4 | 45 | 14 |

EXPERIMENT G

1. Local reactions

In 3 cows with a body weight of 300–450 kg 20 ml of composition VII were injected in the neck muscles of each cow. This corresponds with a dose of 8.3–5.5 mg/kg.

In all animals a short subcutaneous oedema was observed. In the first animal no further reaction developed (−), while the second animal showed some reaction (±). In the third animal a short moderate reaction (+) was observed.

2. Bio-availability (corrected for a dose of 5 mg/kg)

Result:

| Composition | dose mg/kg | n | r | $t_{\frac{1}{2}}$ (h) | $t_{max}$ (h) | $C_{max}$ (mg/kg) |
|---|---|---|---|---|---|---|
| VII | 5 | 3 | −0.99 | 48.0 | 24 | 30 |

EXPERIMENT H

1. Local reactions

In addition to experiment A a clinical trial was carried out with 384 cows with a body weight varying from 400–700 kg. The animals were injected in the neck muscles with composition I in a dose of 3 mg/kg.

In 329 cows no reaction was determined (−), while in 28 animals some hardening of the muscle tissue was observed for 2 days (±). In 11 cows the reaction was visible (+) for 2 days, while in 14 animals a moderate reaction (+ +) was observed for 2 days. Only 2 animals showed a serious reaction (+ + +). Subcutaneous oedema was observed in 3 animals for 2 days.

2. Bio-availability
Not determined.

EXPERIMENT I

1. Local reactions

In order to get information about the influence of the injection site on the local reactions and the bio-availability, 40 cows with a body weight of 500–600 kg were injected with composition I in the muscles of the cossum with a dose of 3 mg/kg.

No reaction was found in 22 animals (−), while 2 cows showed some hardening of the muscle tissue for 7 days (±), 10 animals showed a visible reaction for 2–8 days (+) and 1 animal showed a serious reaction for 2 days (+ + +).

In 8 cows a subcutaneous oedema was observed for 1–8 days.

2. Bio-availability
Result

| Composition | dose mg/kg | n | r | $t_{\frac{1}{2}}$ (h) | $t_{max}$ (h) | $C_{max}$ (mg/kg) |
|---|---|---|---|---|---|---|
| I | 3 | 6 | −0.98 | 51 | 30 | 15 |

EXPERIMENT J

1. Local reactions

In addition to experiment A 20 cows with a body weight of about 500 kg were injected in the neck muscles with composition I in a dose of 5 mg/kg.

No reaction was determined in 12 animals (−), 2 animals showed some hardening of the muscle tissue for 3 days (±), 5 animals showed a visible reaction for 7 days (+), while in 1 cow a moderate reaction was observed for 8 days (+ +).

2. Bio-availability
Result:

| Composition | dose mg/kg | n | r | $t_{\frac{1}{2}}$ (h) | $t_{max}$ (h) | $C_{max}$ (mg/kg) |
|---|---|---|---|---|---|---|
| I | 5 | 6 | −0.97 | 57 | 27 | 29 |

EXPERIMENT K

1. Local reactions

In addition to experiment B 15 cows of about 500 kg were injected in the neck muscles with composition Ii in a dose of 5 mg/kg.

No reaction was found in 5 animals (−), 4 cows showed some hardening of the muscle tissue for 6 days (±), 5 animals showed a visible (+) reaction for 4–8 days, while in 1 animal a moderate reaction (+ +) was observed for 4 days.

2. Bio-availability
Result:

| Composition | dose mg/kg | n | r | $t_{\frac{1}{2}}$ (h) | $t_{max}$ (h) | $C_{max}$ (mg/kg) |
|---|---|---|---|---|---|---|
| II | 5 | 6 | −0.99 | 58 | 30 | 22 |

EXPERIMENT L

1. Local reactions

In addition to experiment B 6 cows with body weight of about 450 kg were injected in the muscles of the cossum with 20 ml of composition II each.

A visible reaction was observed in 1 animal for 3 days (+), while 5 animals showed a moderate reaction for 3–6 days (+ +). Four of these animals showed a hard tubercle for 1–5 days, while in all animals subcutaneous oedema was observed for 2 days.

2. Bio-availability (corrected to 5 mg/kg)
Result:

| Composition | dose mg/kg | n | r | $t_{\frac{1}{2}}$ (h) | $t_{max}$ (h) | $C_{max}$ (mg/kg) |
|---|---|---|---|---|---|---|
| II | 5 | 12 | −0.96 | 59 | 33 | 22 |

The plasma concentration levels of the active compound A in the Experiments were determined as follows.

Blood was collected in heparinized vacuum tubes from the jugular vein. The blood was centrifuged for 15 minutes at 1800. g. From the plasma 2.5 ml was transferred to an extraction tube. If haemolysis had taken place, 50 μl of 30% hydrogen peroxide was added to the plasma. Then 2.5 ml of a 0.5 M solution of citric acid and 8 ml of toluene were added. The tube was closed, shaken vigorously for 30 min. and centrifuged for 3 min. at 1800. g.

From the top layer 6 ml was pipetted into another extraction tube, then the pharmacon was extracted with 1.5 ml of a saturated solution of sodium borate. After separation of the two layers and subsequent centrifugation, the concentration of the active compound A in the water phase was determined spectrophotometrically at 417 nm.

We claim:

1. A pharmaceutical composition for the treatment of distomatosis, comprising an amount, effective against distomatosis, of a member selected from the group consisting of 4,4'-dichloro-6,6'-dinitro-o,o'-bisphenol; 4,4',6,6'-tetrabromo-o,o'-bisphenol; 4,6'-dichloro-4,6'-dinitro-2,2'-methylenediphenol; and 6-bromo-4'-fluoro-4,6'-dinitro-2,2'-methylenediphenol, dissolved in a solvent vehicle comprising 5 to 50 w/v percent of dimethylsulfoxide (DMSO) in combination with a symmetric or unsymmetric ester of adipic acid wherein both alkyl groups together contain six to twelve carbon atoms and wherein the smaller alkyl group present if said ester is unsymmetric contains at least two carbon atoms.

2. A pharmaceutical composition as in claim 1 wherein said ester of adipic acid is di-n-butyl adipate.

3. A pharmaceutical composition as in claim 1 which comprises from 1 to 50% w/v of said therapeutically active material.

4. A pharmaceutical composition as in claim 1 which comprises from 5 to 30% w/v of 4,6'-dichloro-4',6-dinitro-2,2'-methylenediphenol and from 5 to 50% w/v of DMSO in di-n-butyl adipate.

5. A pharmaceutical composition as in claim 4 which contains proportionally 12.5 g of 4,6'-dichloro-4', 6-dinitro-2,2'-methylenediphenol and 30 g of DMSO, completed with di-n-butyl adipate to 100 cm$^3$.

6. The method of treating a mammal suffering from distomatosis which comprises parenterally administering to said mammal an amount, effective against distomatosis, of a pharmaceutical composition as in claim 1.

7. The method of treating a mammal suffering from distomatosis which comprises parenterally administering to said mammal an amount, effective against distomatosis, of a pharmaceutical composition as in claim 4.

8. The method of treating a mammal suffering from distomatosis which comprises parenterally administering to said mammal an amount, effective against distomatosis, of a pharmaceutical composition as in claim 5.

* * * * *